(12) United States Patent
Thompson et al.

(10) Patent No.: US 7,029,850 B1
(45) Date of Patent: Apr. 18, 2006

(54) TRAVERSE SHEAR MODE PIEZOELECTRIC CHEMICAL SENSOR

(75) Inventors: Michael Thompson, Toronto (CA); Gordon L. Hayward, Guelph (CA)

(73) Assignee: SencorChem International Corporation, Toronto (CA)

(*) Notice: Subject to any disclaimer, the term of this patent is extended or adjusted under 35 U.S.C. 154(b) by 414 days.

(21) Appl. No.: 10/089,220

(22) PCT Filed: Sep. 29, 2000

(86) PCT No.: PCT/CA00/01139

§ 371 (c)(1),
(2), (4) Date: Aug. 19, 2002

(87) PCT Pub. No.: WO01/23892

PCT Pub. Date: Apr. 5, 2001

Related U.S. Application Data

(60) Provisional application No. 60/156,714, filed on Sep. 30, 1999.

(51) Int. Cl.
*C12Q 1/68* (2006.01)

(52) U.S. Cl. .................................................. 435/6

(58) Field of Classification Search ............... 435/67.1, 435/174, 283.1; 422/40, 68.1, 82.05; 436/501, 436/283.1, 174
See application file for complete search history.

(56) References Cited

U.S. PATENT DOCUMENTS 6,060,023 A * 5/2000 Maracas ................. 422/68.1
6,287,874 B1 * 9/2001 Hefti ...................... 436/501

OTHER PUBLICATIONS

Čavić et al., "Acoustic waves and the real-time study of biochemical macromolecules at the liquid/solid interface", *Faraday Discussions*, 1997, 107, pp. 159-176.
Ferrante et al., "Molecular slip at the solid-liquid interface of an acoustic-wave sensor", *Journal of Applied Physics*, 76 (6), Sep. 15, 1994, pp. 3448-3462.
Su et al., "Platinum Anticancer Drug Binding to DNA Detected by Thickness-Shear-Mode Acoustic Wave Sensor", *Analytical Chemistry*, vol. 67, No. 5, Mar. 1, 1995, pp. 1010-1013.

* cited by examiner

*Primary Examiner*—Jeffrey Fredman
*Assistant Examiner*—Heather G. Calamita
(74) *Attorney, Agent, or Firm*—Kathleen Marsman; Borden Ladner Gervais LLP

(57) ABSTRACT

The present invention relates to a process for sensing biological or chemical changes in molecular structural shape or mass of molecules attached to the surface of a transverse shear piezoelectric oscillating molecular sensing device driven by a network analyzer. The process comprises the steps of i) exciting the sensor device at a series of predetermined frequencies, ii) collecting data to determine values for the predetermined parameters of series resonance frequency shift (fS), motional resistance (RM), motional inductance (LM), motional capacitance (CM), electrostatic capacitance (Co) and boundary layer slip parameter ($\alpha$); and iii) determining relative changes in the measured parameters to detect thereby any changes in molecular structural shape or mass at sensing device surface.

7 Claims, No Drawings

TRAVERSE SHEAR MODE PIEZOELECTRIC CHEMICAL SENSOR

This appln caims the benefit of 60/156,714 filed Sep. 30, 1999.

FIELD OF THE INVENTION

This invention relates to a process of detecting specific molecules in a liquid (the analyte) with receiving molecules, (the receptors) which are attached to the surface of a thickness shear mode acoustic sensor (TSM). Acoustic energy generated in the sensor is transferred to and from the fluid depending on the surface coupling behaviour. The coupling is altered when the analyte binds to the receptor producing easily measured changes in the electrical characteristics of the sensor.

The invention further relates to the application of the measurement of the coupling effects to the sensing of biomolecules, and other molecules of biological significance such as drugs, in general. For example, the receptor may be a protein, a single oligonucleotide strand, DNA or RNA and the analyte a protein, drug or complementary strands of DNA or RNA. The interaction between the analyte and the sensor bound receptor can be identified through a quantitative TSM response. Other measurement scenarios are possible through the detection of changes in the acoustic coupling between the sensor surface and the surrounding liquid.

BACKGROUND OF THE INVENTION

A TSM sensor is a device which generates mechanical vibrations from an electrical signal and uses these vibrations to detect and/or quantify particular chemical or biochemical substances present in a medium surrounding the sensor (the analyte). Acoustic energy is stored and dissipated both in the device itself, and through interfacial coupling, in a surrounding liquid medium. By coating the sensor with one or more layers of a substance which interacts with the analyte, the energy storage and transfer processes change when the interaction occurs. This changes the acoustic resonance of the sensor, which can be observed by measuring the electrical impedance of the sensor. The applicants have published several papers in this field and they are listed as follows:

1.) F. Ferrante, A. L. Kipling and M. Thompson, "Molecular Slip At The Solid-Liquid Interface Of An Acoustic Wave Sensor", *J. Appl. Phys.* 76(6):3448–3462, 1994;
2) G. L. Hayward and M. Thompson, "A Transverse Shear Model Of A Piezoelectric Chemical Sensor", *Amer. Inst. Physics* 83(40:2194–2201, 1998;
3) Cavic B. A. et al., "Acoustic Waves And The Real-Time Study Of Biochemical Macromolecules At The Liquid/Solid Interface", *Faraday Discuss.* 107:159–176, 1997;
4) H. Su and M. Thompson, "Rheological And Interfacial Properties Of Nucleic Acid Films Studies By Thickness-Shear Mode Sensor And Network Analysis", *Can. J. Chem.* 74:344–358, 1996.

There are several mechanisms whereby a TSM sensor responds to chemical change on its surface when it is immersed in a liquid. Surface mass deposition occurs when the analyte binds to the receptor on the sensor surface. This increases the storage of acoustic energy through the inertia of the added mass. Acoustic energy may also be stored through the elastic deformation of a coating on the surface. The elasticity of the coating may also change when the analyte binds to the receptor coating. These energy storage modes determine the resonant characteristics of the sensor which can easily be measured electrically. These processes are well known. Examples of piezoelectric sensors are described, for example in U.S. Pat. Nos. 5,374,521 and 5,658,732.

Viscous loading occurs when acoustic energy is transferred to the liquid. Some of the acoustic energy is stored by the inertia of the fluid moving with the sensor surface and can be transferred back to the sensor, but acoustic energy is also dissipated by internal friction within the fluid. The viscous loading effect is also well known, however in the current use of this effect, the transfer of acoustic energy at the surface is considered to be perfect, that is, there is no slip between the sensor surface and the adjacent fluid molecules.

The current practice is based on the well known Butterworth—van Dyke model of a piezoelectric resonator which consists of a resistor, inductor and capacitor in series, all in parallel with another capacitor. The series arm of this network is called the motional arm. Further details of this model and the calculation of the following parameters may be found in the above paper entitled "Rheological and Interfacial Properties of Nucleic Acid Films Studies by Thickness-Shear Mode Sensor and Network Analysis".

Motional Inductance

The motional inductance, $L_M$, represents the inertial energy stored by the sensor. It depends on the mass of the TSM sensor as well as the mass of material (the analyte) added to the surface. Since liquid coupled to the surface can store and return acoustic energy, $L_M$ is also dependent on the viscosity of the liquid.

Motional Resistance

The motional resistance, $R_M$, is intrinsically related to the energy dissipated by the sensor.

Accordingly, any imposition of material (or loss of material) that has a viscous property or changes in the viscosity of the liquid will result in a change in the energy dissipation and hence $R_M$.

Motional Capacitance

The motional capacitance, $C_M$, represents the elastic energy stored by the sensor. The absorption or chemical binding of the analyte to the coating can have a large effect on the viscoelastic properties of the coating. Depending on the thickness, an added (or removed) layer of material may change the elasticity of the sensor and thus affect $C_M$. Although most fluids are considered to be viscous, at the high frequencies used in piezoelectric quartz sensors, the liquid may also have elastic properties.

Static Capacitance

The static capacitance $C_O$ represents the dielectric constant of the quartz, but includes that of the medium through the electric field. Charge interactions between the analyte and the sensor coating will affect this value.

SUMMARY OF THE INVENTION

According to an aspect of the invention, there is provided a process for sensing biological or chemical changes in molecular structural shape or mass of molecules attached to the surface of a transverse shear piezoelectric oscillating molecular sensing device driven by a network analyzer, said process comprising:

i) exciting said sensor device at a series of predetermined frequencies;

ii) collecting data to determine values for the predetermined parameters of series resonance frequency shift (fS), motional resistance (RM), motional inductance (LM), motional capacitance (CM), electrostatic capacitance (Co) and boundary layer slip parameter ($\alpha$); and iii) determining relative changes in said measured parameters to detect thereby any changes in molecular structural shape or mass at sensing device surface.

In accordance with another aspect of the invention there is provided a method of determining the efficiency of acoustic coupling between a sensor and the surrounding fluid, said method comprising:

a) applying an electrical signal of known frequency and voltage to the sensor;

b) measuring the current through the sensor to determine the impedance at the known frequency;

c) repeating steps a) and b) over a range of frequencies to generate a set of impedance data; and d) fitting the measured impedance data to determine an $\alpha$ parameter which represents coupling strength.

DETAILED DESCRIPTION OF THE PREFERRED EMBODIMENTS

This invention is based on the measurement of phenomena based on imperfect acoustic coupling between the sensor surface and the liquid. The nature of this coupling determines the strength of the viscous loading and elastic effects depending on such parameters as the surface free energy and the molecular conformation of the sensor coating. These molecular parameters are very sensitive to chemical changes at the surface and therefore acoustic coupling provides a novel sensing mechanism.

The impedance measurements are carried out by applying an electrical signal of known frequency and voltage to the sensor and measuring the current through the sensor. Through Ohm's law, this provides the impedance at the known frequency. By performing this measurement over a range of frequencies, a set of data is generated. The above described, specifically selected parameters of $L_M$, $R_M$, $C_M$, and $C_O$ have been found to be the determining parameters for indicating a mass or conformation change at the TSM surface. Hence these parameters are fitted to the data.

While the Butterworth—van Dyke model provides useful information, it is an electrical analogy which presents the information unclearly. An alternate model of the TSM sensor is based on a solution of the equations of motion and electric fields. With this second model as set out in the aforementioned paper entitled "Molecular Slip At The Solid-Liquid Interface Of An Acoustic Wave Sensor" and "A Transverse Shear Model Of A Piezoelectric Chemical Sensor", the deposited mass and the coupling may be determined directly by fitting the electrical impedance data obtained as above. The coupling is represented by a slip parameter, $\alpha$, which arises from a slip boundary condition used in solving the set of equations. The common approach is to assume perfect coupling and to set $\alpha=1$. In this invention, $\alpha$ is taken to be a complex number which is determined by fitting the measured impedance data.

The sensing process is understood to be occurring at the interface between the solid device and the liquid medium. Ligands for biological macromolecules include small molecules, ions, proteins, peptides, and strands of both DNA and RNA. The interaction of these entities with the biological molecules attached to the sensor will cause an alteration of the physical properties of the film resulting, in turn, in changes in the measured parameters. These changes will very clearly result from a combination of some or all of the above response mechanisms particular for each chemical situation. In this regard, the dimensions of the newly bound ligand is an important consideration.

The signaling species coated onto the acoustic biosensor are proteins (antibodies, enzymes, hormones, molecular receptors, etc.) and nucleic acids oligonucleotides, DNA and RNA) attached to the device surface. These molecules exist in a highly hydrated form which can be considered to constitute very viscous gels.

The effect of viscous loading is the result of acoustic energy transfer to and from the surrounding medium. This in turn depends on the nature of the contact between the surface and the medium. The contact is controlled by such chemical properties as hydrogen bonding, dispersion interactions and interfacial charge. The process can be viewed as a drag existing between the surface coating and the liquid. $\alpha$ represents the coupling strength but also contains phase shift information. This provides additional information regarding relative mass of liquid molecules compared to those of the sensor surface and when correlated with the selected Butterworth—van Dyke model provide a determination on what is happening at the TSM surface, namely, mass and/or molecular structural shift or change in conformation.

EXAMPLE

The human immunodeficiency virus type I (HIV-I) is strongly regulated at the transcriptional level by the interaction of an 86-amino acid protein, Tat, with the trans activation responsive element at the 5'-end of the viral messenger RNA transcript (TAR). The TAR-Tat system is an important target for drug discovery research because the binding of the regulatory protein to TAR can be blocked by small molecules.

In this application we compute the slip parameter $\alpha$, for the binding of Tat-derived peptides to TAR immobilized on a sensor surface. The TAR RNA is synthesized, with a biotin moiety at the 5'-end, on a DNA synthesizer by standard phosphoramidite chemistry. The acoustic wave sensor is incorporated into a flow-through configuration and electrically connected to an acoustic network analyzer. A dispersion of 100–500 μl of the reagent neutravidin is injected into the apparatus and the protein adsorbs to the gold electrode surface of the acoustic wave sensor. A dispersion of biotinylated TAR-RNA (100–500 μl) is introduced into the system where the formation of the biotin-avidin complex results in attachment of TAR to the sensor surface. Various Tat-derived peptides are then introduced into the flow-trough system. In this particular application the following peptides are specified: $tat_{12}$, $tat_{20}$, and $tat_{30}$ where the subscript refers to the number of amino acids in the peptide. Dispersions of peptide (100–500 μl) are injected into the system. On binding of peptide to TAR in real time transient responses in the aforementioned parameters are obtained. The computed $\propto$ parameter for the various responses, which distinguishes the nature on binding, are as follows:

$Tat_{12}$ baseline 1.978 @ 20.85 degrees
signal 1.964 @ 20.97 degrees
$Tat_{20}$ baseline 1.985 @ 21.42 degrees
signal 1.926 @ 18.15 degrees
$Tat_{30}$ baseline 1.982 @ 22.61 degrees
signal 1.994 @ 23.03 degrees $Tat_{12}$ displays a small decrease in slip magnitude with an increase in phase, whereas $tat_{20}$ shows large decreases in magnitude and phase. $Tat_{30}$ depicts smaller increase in magnitude and phase.

Although preferred embodiments of the invention have been described herein in detail, it will be understood by those skilled in the art that variations may be made thereto without departing from the spirit of the invention or the scope of the appended claims.

What is claimed is:

1. A process for sensing a chemical change in molecular conformation or mass of a biomolecule attached to the surface of a transverse shear piezoelectric sensing device driven by a network analyser, said change being attributable to a binding interaction between said biomolecule attached to the surface and a biological entity in a surrounding liquid medium upon exposure of the surface to the surrounding liquid medium, said process comprising the steps of:
   i) exciting said sensing device at a series of predetermined frequencies prior to and during exposure to the surrounding liquid medium;
   ii) collecting data from the sensing device to determine values for parameters: series resonance frequency shift (fS), motional resistance (Rm), motional inductance (Lm), motional capacitance (Cm), electrostatic capacitance (Co), and boundary layer slip parameter ($\alpha$);
   iii) determining a relative change in said parameters in step ii) upon exposure of the surface to the surrounding liquid medium; and
   iv) correlating the relative change in said parameters determined in step iii) with a calibrated set of data for said parameters to determine a change in molecular conformation or mass of the biomolecule attached to the surface attributable to a binding interaction upon exposure to the surrounding liquid medium;
   wherein a change in boundary layer slip parameter ($\alpha$) and an essentially zero change in the series resonance frequency shift (fS) confirms a change in molecular conformation and essentially zero change in mass of the biomolecule attached to the surface.

2. The process according to claim 1 wherein said biomolecule attached to the surface is selected from the group consisting of proteins and nucleic acids.

3. The process according to claim 2 wherein said proteins are selected from the group consisting of antibodies, enzymes, molecular receptors, receptor ligands and polypeptides.

4. The process according to claim 2 wherein said nucleic acids are selected from the group consisting of DNA, RNA and oligonucleotides.

5. The process according to claim 1 wherein said biological entity in said surrounding liquid medium is selected from the group consisting of proteins and nucleic acids.

6. The process according to claim 5 wherein said proteins are selected from the group consisting of antibodies, enzymes, molecular receptors, receptor ligands and polypeptides.

7. The process according to claim 5 wherein said nucleic acids are selected from the group consisting of DNA, RNA and oligonucleotides.

* * * * *

UNITED STATES PATENT AND TRADEMARK OFFICE
CERTIFICATE OF CORRECTION

PATENT NO. : 7,029,850 B1
APPLICATION NO. : 10/089220
DATED : April 18, 2006
INVENTOR(S) : Michael Thompson and Gordon L. Hayward It is certified that error appears in the above-identified patent and that said Letters Patent is hereby corrected as shown below:

On Title Page, Col. 1

In item (73) in the bibliographical data, delete "SencorChem International" and insert therefor --SensorChem International--.

Signed and Sealed this

Seventh Day of November, 2006

JON W. DUDAS
*Director of the United States Patent and Trademark Office*